(12) United States Patent
Min et al.

(10) Patent No.: US 8,145,302 B1
(45) Date of Patent: Mar. 27, 2012

(54) METHOD AND SYSTEM TO ESTIMATE DEFIBRILLATION THRESHOLDS

(75) Inventors: Xiaoyi Min, Thousand Oaks, CA (US);
Gene A. Bornzin, Simi Valley, CA (US);
Fujian Qu, Sunnyvale, CA (US)

(73) Assignee: Pacesetter, Inc., Sylmar, CA (US)

( * ) Notice: Subject to any disclaimer, the term of this patent is extended or adjusted under 35 U.S.C. 154(b) by 36 days.

(21) Appl. No.: 12/912,573

(22) Filed: Oct. 26, 2010

(51) Int. Cl.
*A61N 1/00* (2006.01)
(52) U.S. Cl. .......................................... 607/5
(58) Field of Classification Search ............. 600/510; 607/5, 7, 8, 14, 28
See application file for complete search history.

(56) References Cited

U.S. PATENT DOCUMENTS

| | | | |
|---|---|---|---|
| 5,564,422 A | 10/1996 | Chen et al. | |
| 5,954,753 A | 9/1999 | Alt et al. | |
| 6,675,042 B2 | 1/2004 | Swerdlow et al. | |
| 7,194,304 B1 | 3/2007 | Bornzin et al. | |
| 2002/0133206 A1* | 9/2002 | Daum et al. | 607/14 |
| 2010/0023073 A1 | 1/2010 | Belk et al. | |

* cited by examiner

*Primary Examiner* — George Manuel
*Assistant Examiner* — Robert Wieland

(57) ABSTRACT

A method and system are provided to determine a defibrillation threshold (DFT). The method and system determine local conduction (LC) information for at least one LV region of the heart, and designate a ULV pacing electrode, where the ULV pacing electrode is located proximate to a region of the heart for which the LC information satisfies a predetermined LC characteristic. The method and system pace the heart from the ULV pacing electrode such that the region of the heart, for which the LC information satisfies the predetermined LC characteristic, becomes re-polarized early in a repolarization phase following pacing of the heart. The method and system deliver a ULV shock, obtain upper limit of vulnerability (ULV) information based on a heart response to the ULV shock; and obtain a DFT based on the ULV information.

20 Claims, 9 Drawing Sheets

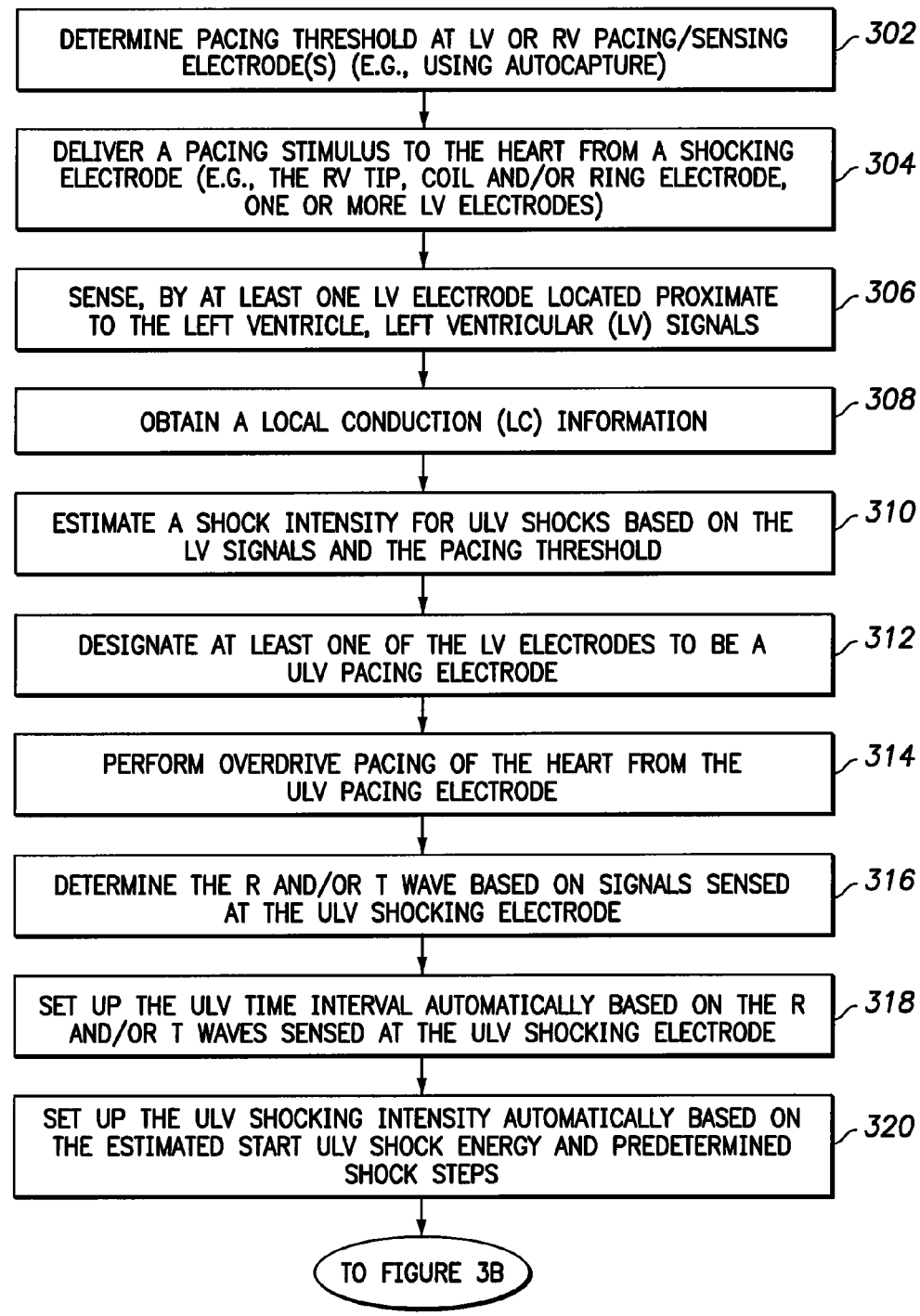

METHOD AND SYSTEM TO ESTIMATE DEFIBRILLATION THRESHOLDS

BACKGROUND OF THE INVENTION

Embodiments generally relate to methods and systems for estimating defibrillation thresholds (DFTs), and more particularly to estimating DFTs based on an upper limit of vulnerability.

Numerous devices and systems exist today that monitor and treat abnormal behavior of the heart (arrhythmias). Examples of arrhythmias include tachycardia, ventricular fibrillation, atrial fibrillation and the like. In general, a device that stops tachycardia and fibrillation of the heart does so by delivering an electrical counter shock to all or a portion of the heart through one or more leads implanted within or proximate to the outer surface of the heart. The electrical shock delivered by the device depolarizes the heart in order to break an abnormal rhythmic cycle and provide an opportunity for the heart to reestablish a normal sinus rhythm. To be successful, the device must deliver an electrical shock that is sufficiently strong to exceed a defibrillation threshold.

When an implantable medical device and the associated lead or leads are implanted, a protocol is followed to determine a defibrillation threshold (DFT) for the patient. The DFT represents the amount of energy needed to effectively defibrillate or cease a tachycardia event and is dependent in part on the implanted lead configuration, the placement of the implanted leads, the individual heart responsiveness to electrical counter shocks and the like.

Methods and systems have been proposed in the past to determine the DFT. One prior DFT determination protocol attempts to predict the defibrillation threshold energy based on a determination of the upper limit of vulnerability (ULV) level for the patient. The ULV level represents an energy strength at which ventricular fibrillation is not induced when the electrical shock is delivered during the vulnerable phase of the cardiac cycle. The vulnerable phase generally is at a time interval near the T wave.

The conventional protocol searches for the ULV level by delivering ULV shocks at various times during the period of vulnerability relative to the T wave. The ULV shocks are delivered at predetermined time intervals prior to or after the peak of the T wave. If the first ULV shock fails to induce ventricular fibrillation, the next test shock may be delivered during a subsequent cardiac cycle at the same strength, but at a different interval relative to the peak of the T wave. This process is repeated for a desired number of time intervals relative to the peak of the T wave. If ventricular fibrillation is not induced after any of the desired ULV shocks, the shock strength is decreased by a set amount and a new group of ULV shocks are delivered in successive cardiac cycles at the predetermined time intervals relative to the peak of the T wave. This process is repeated until fibrillation is induced one or more times. The upper limit of vulnerability represents the ULV level at which fibrillation was induced by a shock delivered during the period of vulnerability.

Conventional protocols that estimate DFTs based on the ULV level have experienced certain limitations. First ULV based estimates generally require inducement of one or more fibrillation events which is not desirable. Also, the ULV level may not be near the DFT, particularly for patients with high DFTs.

Generally, a relation exists between the ULV and the DFT and the associated variables (e.g., shock timing relative to the T wave, shock wave form, electrode configuration, pacing beat and intrinsic conduction). In many patients, the ULV level may closely correlate with the DFT. However, in certain patients, the ULV level may differ significantly from the DFT, such as by 20 Joules and the like. In patients where the ULV and DFT significantly differ, such patients exhibited very unhealthy myocardial characteristics, such as having very low ejection fractions, dilated left ventricles and/or left ventricular hypertrophy. Conventional ULV based DFT estimates have not taken into consideration electrical field distribution and local conduction information.

Generally, fibrillation may be terminated when a majority of the myosites (e.g., a critical mass) of the heart are synchronized by a stimulus. Each stimulus propagates across the heart and exhibits a particular electrical field distribution. The electrical field distribution may be characterized in part by local conduction information, such as the local voltage gradients exhibited at different regions of the heart. The voltage gradient may be characterized as a voltage difference per unit distance across a region of the heart. Different regions of the heart exhibit different voltage gradients. When a shock is delivered from an RV lead through electrodes in the right ventricle, the region of the heart wall proximate to the RV electrode will generally exhibit a higher voltage gradient, as compared to regions of the heart wall that are more remote from the RV electrode. Thus for example, when an RV tip, ring or coil electrode deliver a high energy shock, the heart wall region surrounding the right ventricle that is proximate to the shocking electrode will exhibit high voltage gradients; whereas the right atrial wall, left ventricular wall and left atrial wall will exhibit different voltage gradients that are typically less than the voltage gradients experienced across the right ventricular wall.

Different field distributions are created by different lead configurations, therapy sites and pacing/shocking schemes. For example, when a pacing pulse is delivered near the apex of the RV, one field distribution of voltage gradients will result. When a pacing pulse is delivered near the AV node or near the SVC, second and third different field distributions of voltage gradients will result. The field distribution affects the starting region of depolarization, progression of depolarization and the ending region of depolarization.

Differences in the timing of repolarization for ventricular cells in different regions of the heart depend on the pacing sites and intrinsic beats that occur. During sinus beats in a normal heart, depolarization waves spread in the Purkinje system rapidly and the posterior LV free wall depolarizes last within a cardiac cycle, thereby being marked as the S wave within an ECG signal. When abnormal conduction exists, such as when a left bundle branch block (LBBB) occurs or when an infarction in the left ventricle exists, the time delay of depolarization in the left ventricle increases. The region depolarized last within the cardiac cycle will repolarize last. Similarly, the region depolarized first in the cardiac cycle will repolarize first. The locations of the regions that depolarize and repolarize first and last in the cardiac cycle vary based on, among other things, the pacing sites.

As noted above, at least one conventional protocol has been provided that finds the ULV by shocking at various test intervals based on the peak of the T wave and at predetermined stepped energy levels. The conventional protocol, during the ULV testing, pacing pulses are delivered by an RV or RA electrode. The paced pulses are delivered in the same region of the heart where a subsequent ULV shock is delivered. The field distribution, that is initiated by an RV or RA pacing pulse, propagates from the RV or RA electrode outward across the heart. This conventional protocol has certain limitations. Delivering paced pulses in the same region where the ULV shocks are delivered may not yield a desired repolarization timing sequence. For example, in the conventional protocol, when the patient exhibits slow conduction or left bundle branch block to the LV, the LV free wall will repolarize last. During a ULV test shock delivered relative to the peak of the T wave, part of the ventricular cells in the LV free wall will still be in the refractory state. If the LV free wall is in a refractory state when a ULV test shock is delivered, the heart may be less vulnerable to the ULV shock and thus not enter a fibrillation state. This will lead to an unduly low ULV that is determined, much lower that the DFT in patients that exhibit dilated left ventricles or left ventricular hypertrophy or slow conduction due to some other myocardial conditions.

Embodiments are described herein that seek to provide new and more reliable methods and systems for determining the ULV and in turn, better estimate the DFT which will reduce ventricular fibrillation induction and simplify implantation procedures. Embodiments are described herein that seek to provide new methods and systems that afford a first order estimation of the DFT without the need to induce any arrhythmia.

SUMMARY

In accordance with one embodiment, a method and system are provided that pace in the low voltage gradient region of the shocking vector in order to determine the upper limit of vulnerability. In accordance with one embodiment, a method and system are provided in which an LV electrode is used to pace before an RV electrode is used to deliver ULV shocks in order to determine the ULV. In accordance with one embodiment, a method and system are provided that use multiple LV electrodes on a LV lead to afford multiple options for ULV pacing in connection with a ULV determination process. In accordance with one embodiment, a method and system are provided that estimate DFT without inducing fibrillation as a first order approximation. The DFT estimation uses sensed amplitude at sensing electrodes when pacing pulses are delivered from shock coils and pacing thresholds at the corresponding sensing site.

In accordance with one embodiment, a method is provided to determine a defibrillation threshold (DFT). The method includes determining local conduction (LC) information for at least one LV region of the heart, and designating a ULV pacing electrode. The LC information is associated with a region along a defibrillation vector that extends between the defibrillation electrodes. The ULV pacing electrode is located proximate to a region of the heart for which the LC information satisfies a predetermined LC characteristic. The method includes pacing the heart from the ULV pacing electrode such that the region of the heart, for which the LC information satisfies the predetermined LC characteristic, becomes re-polarized early in a repolarization phase following pacing of the heart. The method further includes delivering a ULV shock, obtaining upper limit of vulnerability (ULV) information based on a heart response to the ULV shock; and obtaining a DFT based on the ULV information.

In accordance with one embodiment, the determining operation includes calculating at least one local gradient associated with at least one region of the heart. Optionally, the determining operation may calculate at least one local gradient that represents voltage per unit distance. The ULV and DFT may be obtained without inducing fibrillation. Optionally, the method may include delivering a stimulus to the heart and sensing, by at least one LV electrode located proximate to the left ventricle, left ventricular signals that are responsive to the stimulus delivered to the heart.

In accordance with one embodiment, a ULV time interval is set relative to a feature of interest in the cardiac cycle. Optionally, the ULV pacing electrode represents an LV electrode located proximate to the region of the left ventricle that exhibits a lowest voltage gradient. The measuring operation includes determining a local voltage difference between at least a pair of LV electrodes. The measuring operation may obtain the LC information based on LV signals sensed by LV electrodes. The LV region of the heart for which the LC information is measured may be located along a defibrillation shocking vector in the posterior or anterior LV free wall. The LC information may be measured utilizing a multi-electrode LV lead. The method may include delivering a low energy pulse to at least one of an LV apex and an LV free wall. The ULV time interval may be set with respect to a peak of a T wave.

In accordance with one embodiment, a system is provided to determine a DFT that comprises an input to receive left ventricular signals measured by an LV electrode and a processor module. The processor module is configured to determine local conduction information for at least one LV region of the heart based on the LV signals measured. A ULV pacing electrode is located proximate to a region of the heart for which the LC information satisfies a predetermined LC characteristic. The processor module is configured to control pacing of the heart from the ULV pacing electrode such that the region of the heart, for which the LC information satisfies the predetermined LC characteristic, becomes re-polarized early (e.g., first) in a repolarization phase following pacing of the heart. The processor module is configured to control delivery of a ULV shock, to obtain upper limit of vulnerability information based on a heart response to the ULV shock, and to obtain a DFT based on the ULV information.

In accordance with an embodiment, the processor module calculates at least one local gradient associated with at least one region of the heart. The ULV and DFT are obtained without inducing fibrillation. A shocking electrode delivers a stimulus to the heart. At least one LV electrode is located proximate to the left ventricle to sense LV signals that are responsive to the stimulus delivered to the heart. The processor module sets a ULV time interval relative to a feature of interest in the cardiac cycle. The ULV pacing electrode represents an LV electrode located proximate to the region of the left ventricle that exhibits a local voltage gradient that satisfies the predetermined LC characteristic.

BRIEF DESCRIPTION OF THE DRAWINGS

FIGS. 3A and 3B illustrate a flow chart for a processing sequence carried out in accordance with an embodiment.

DETAILED DESCRIPTION

Figure 1A:
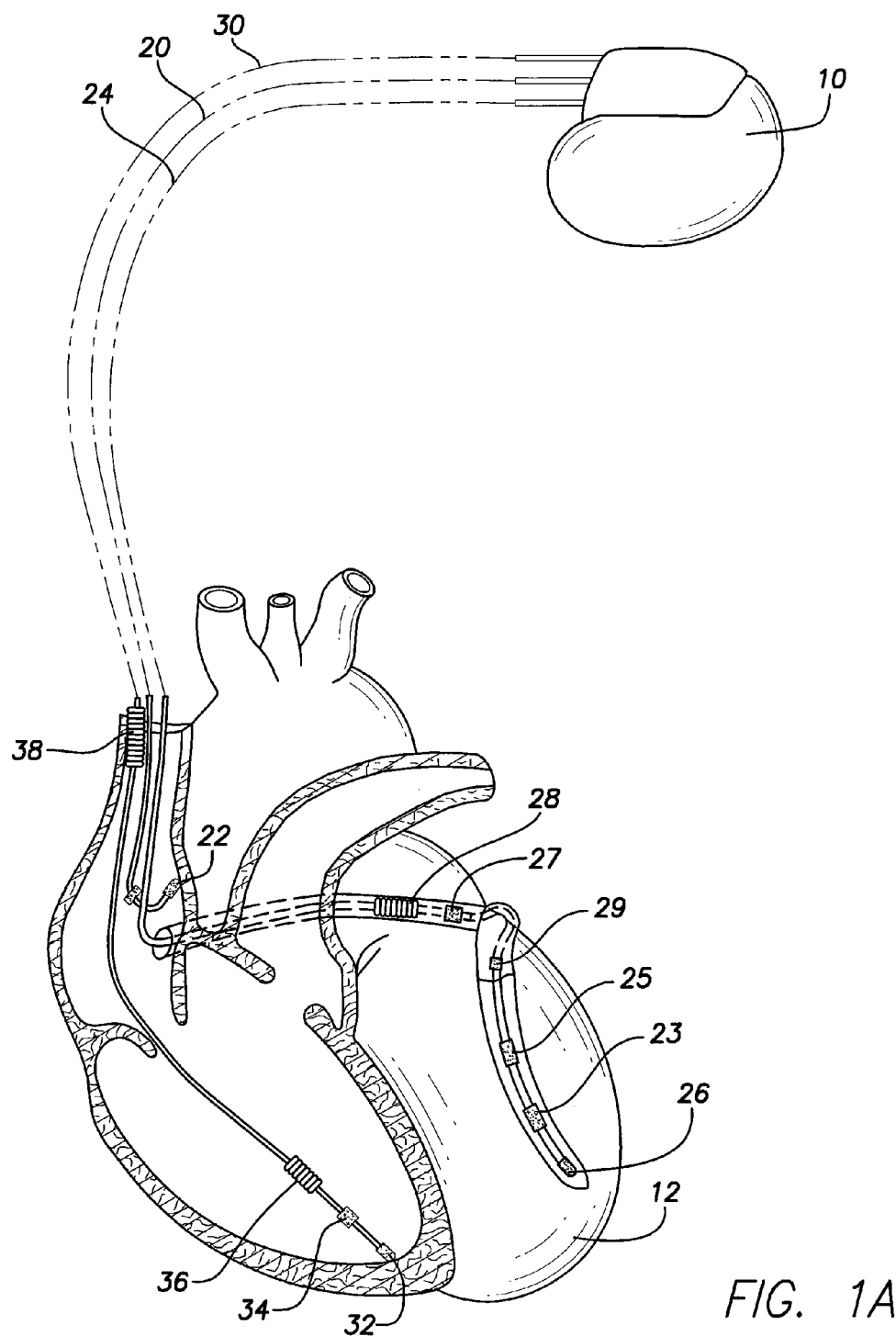
FIG. 1A illustrates a simplified diagram of an implantable stimulation device for estimating DFTs in accordance with an embodiment.

FIG. 1A illustrates a simplified diagram of an implantable medical device 10 in electrical communication with at least three leads 20, 24 and 30 implanted in or proximate a patient's heart 12 for delivering multi-chamber stimulation (e.g. pacing, ATP therapy, high voltage shocks and the like) according to an embodiment. The stimulation includes defibrillation shocks that are delivered along one or more defibrillation shocking vectors, such as between an RV electrode and a CAN electrode or between RV, SVC and CAN electrodes. The device 10 is also configured to perform ULV based estimation of the DFT based on local conduction information collected along a defibrillation vector and utilizing LV electrodes. As explained below, the leads 20, 24 and 30 are used to sense VT and VF and to deliver, among other things, anti-tachycardia and defibrillation shocks. The device 10 is programmable, by an operator, to set certain operating parameters, as well as therapy-related parameters. The device 10 is configured to operate with various configurations of leads. Exemplary lead configurations are shown in the Figures. The device 10 is configured to deliver various types of therapies.

To sense atrial cardiac signals and to provide right atrial chamber stimulation therapy, the medical device 10 is coupled to an implantable right atrial lead 20 having at least an atrial tip electrode 22, which typically is implanted in the patient's right atrial appendage. The implantable medical device 10 may be a pacing device, a pacing apparatus, a cardiac rhythm management device, an implantable cardiac stimulation device, an implantable cardioverter/defibrillator (ICD) and/or a cardiac resynchronization therapy (CRT) device.

To sense left atrial and ventricular cardiac signals and to provide left chamber pacing therapy, the medical device 10 is coupled to an LV lead 24. The LV lead 24 may receive atrial and ventricular cardiac signals and deliver left ventricular pacing therapy using a left ventricular (LV) tip electrode 26, and intermediate LV electrodes 23, 25 and 29. Left atrial pacing therapy uses, for example, first and second left atrial (LA) electrodes 27 and 28. The LV and LA electrodes 23-29 may represent sensing sites, where cardiac signals are sensed, and/or may represent pacing and/or shock therapy sites. A right ventricular lead 30 includes an RV tip electrode 32, an RV ring electrode 34, an RV coil electrode 36, and a superior vena cava (SVC) coil electrode 38 (also known as a RA coil electrode). The right ventricular lead 30 is capable of sensing cardiac signals, and delivering stimulation in the form of pacing and shock therapy to the SVC and/or right ventricle.

Embodiments are described herein, whereby multiple LV electrodes are utilized to sense cardiac activity at multiple LV sensing sites in order to measure LC information along defibrillation vectors, such as the local voltage gradient for associated regions of the heart. Information collected at the sensing sites (e.g., LV alone or LV and RV, RA and/or LA) is utilized to determine sites, at which ULV pacing should be delivered. The information may also be used to determine initial ULV shock strength and/or DFT estimates. In certain embodiments, multiple LV electrodes are utilized to deliver pacing pulses at one or more LV sites and along one or more pacing vectors.

Figure 1B:
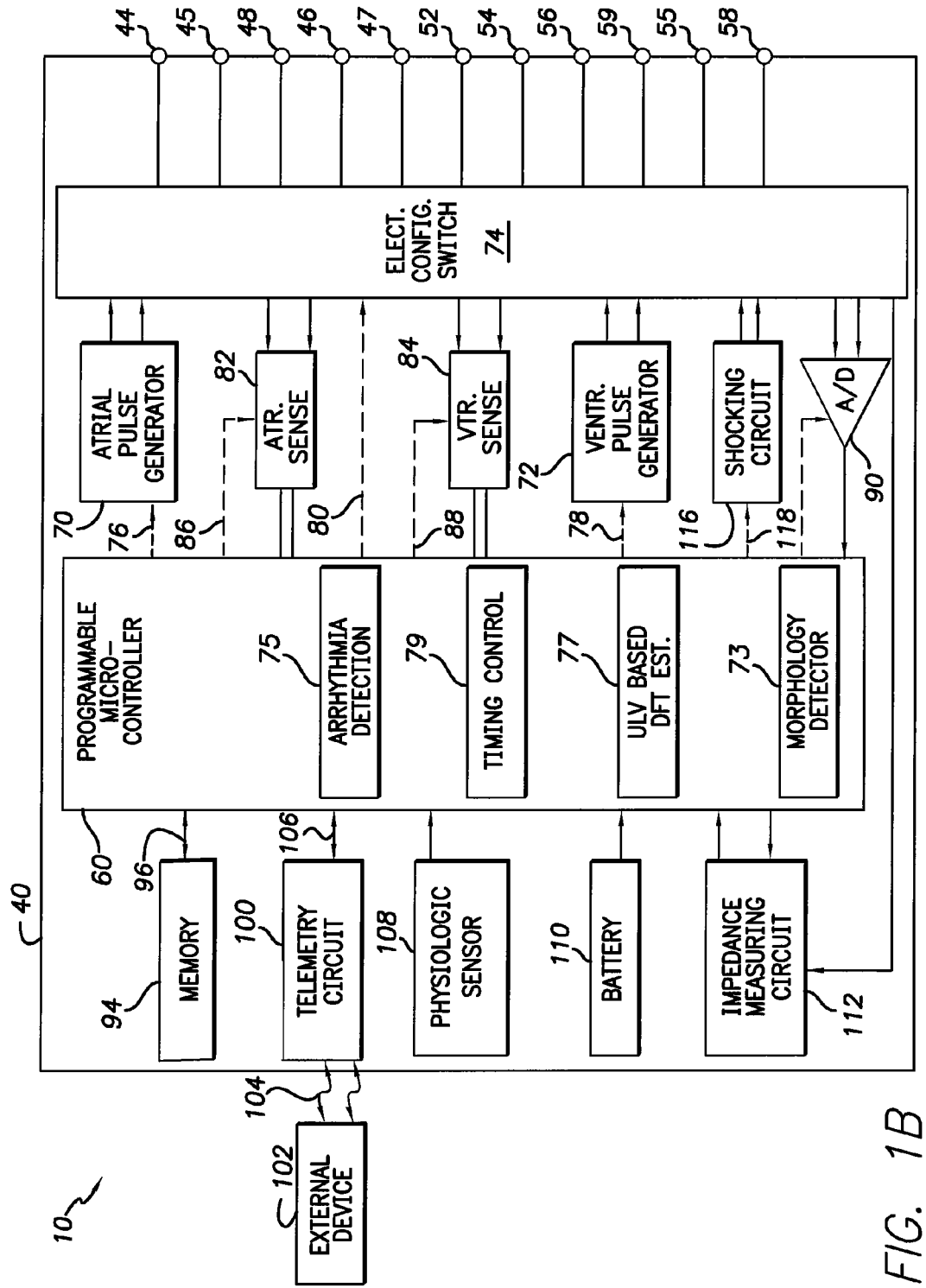
FIG. 1B illustrates a functional block diagram of the device of FIG. 1 in accordance with an embodiment.

FIG. 1B illustrates a block diagram of the stimulation device 10, which is capable of treating both fast and slow arrhythmias with stimulation therapy, including cardioversion, defibrillation, and pacing stimulation. While a particular multi-chamber device is shown, this is for illustration purposes only. It is understood that the appropriate circuitry could be duplicated, eliminated or disabled in any desired combination to provide a device capable of treating the appropriate chamber(s) with cardioversion, defibrillation and pacing stimulation.

The housing 40 for the stimulation device 10, shown schematically in FIG. 1B, is often referred to as the "can", "case" or "case electrode" and may be programmably selected to act as the return electrode for some or all "unipolar" modes. The housing 40 may further be used as a return electrode alone or in combination with one or more of the coil electrodes, 29, 36 and 38 of FIG. 1, for shocking purposes. The housing 40 further includes a connector (not shown) having a plurality of terminals, 44, 45, 46, 47, 48, 52, 54, 55, 56, 58, and 59. To achieve sensing, pacing and shocking in desired chambers of the heart, the terminals 44-59 are connected to corresponding combinations of electrodes 22-36.

An electrode configuration switch 74 connects the sensing electronics to the desired ones of the terminals 44-59 of corresponding sensing electrodes. For example, terminals 55-59 may be coupled to LV electrodes 23, 25, 26 and 29. The switch 74 may connect terminals 55-59 to one or more ventricular sensing circuits 84, which provide signals, representative of cardiac activity, to the microcontroller. The circuit 84 may amplify, filter, digitize and/or otherwise process the sensed signals from the LV electrodes 23, 25, 26 and 29. The circuit 84 may provide separate, combined or difference signals to the microcontroller 60 representative of the sensed signals from the LV electrodes 23, 25, 26 and 29. The circuit 84 may also receive sensed signals from RV electrodes. The atrial sensing circuit 82 is connected through the switch 74 to desired RA and/or LA electrodes to sense RA and/or LA cardiac activity.

The stimulation device 10 includes a programmable microcontroller 60 that controls the various modes of ULV testing and stimulation therapy. The microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. The microcontroller 60 includes the ability to process or monitor input signals (data) as controlled by a program code stored in memory. The details of the design and operation of the microcontroller 60 are not critical to the present invention. Rather, any suitable microcontroller 60 may be used.

The microcontroller 60 searches for a pacing threshold following paced events. The microcontroller 60 may do so, by performing an auto capture process to determine whether a paced event successfully captured the surrounding tissue. The microcontroller 60 also includes a ULV-based DFT estimation module 77. The module 77 determines local conduction (LC) information for at least one LV region of the heart. The module 77 designates a ULV pacing electrode, where the ULV pacing electrode is located proximate to a region of the heart for which the LC information satisfies a predetermined LC characteristic. For example, module 77 may calculate one or more local gradients associated with at least one region of the heart and calculate at least one local gradient that represents voltage per unit distance. The microcontroller 60 paces the heart from the ULV pacing electrode such that the region of the heart, for which the LC information satisfies the predetermined LC characteristic, becomes re-polarized early (e.g., first) in a repolarization phase following pacing of the heart and delivers a ULV shock as compared to re-polarization of other regions of the heart. The module 77 obtains ULV information based on a heart response to the ULV shock. The ULV information may be the ULV shock intensity at which the heart enters a fibrillation state. The module 77 may measure the level of an evoked response at the LV electrode(s) following delivery of the ULV shock at the ULV shocking electrode, with the ULV information including a ratio of the voltage levels of the ULV shock to the measured LV signal. As yet another example, the module 77 may measure the voltage gradient at the LV electrode(s) following delivery of the ULV shock at the ULV shocking electrode with the ULV information including the ratio of the measured voltage gradient at the LV electrode(s) to a baseline voltage gradient.

The module 77 obtains a DFT based on the ULV information. In certain embodiments, the ULV and DFT are obtained without inducing fibrillation. To determine the LC information, the microcontroller 60 delivers a stimulus to the heart and the module 77 senses by at least one LV electrode located proximate to the left ventricle, LV signals that are responsive to the stimulus delivered to the heart. The ULV pacing electrode represents an LV electrode located proximate to the region of the left ventricle that exhibits a local voltage gradient that satisfies the predetermined LC characteristic (e.g., lowest voltage gradient). The module 77 determines a local voltage difference between at least a pair of LV electrodes and obtains the LC information based on LV signals sensed by LV electrodes. The microcontroller 60 includes an arrhythmia detection module 75 that analyzes sensed signals and determines when an arrhythmia (e.g., fibrillation) is occurring. The detection module 75 receives signals sensed by electrodes located at sensing sites. For example, the signals may be received from multiple LV electrodes which represent cardiac activity at the corresponding multiple LV sensing sites. The detection module 75 detects an arrhythmia that represents at least one of a tachycardia and fibrillation, such as ventricular tachycardia (VT) and ventricular fibrillation (VF). The microcontroller 60 includes a morphology detection module 73 that analyzes a morphology of the cardiac signal. Among other things, the module 73 may detect R wave peaks and/or detect T wave features of interest, such as onset, peak, etc.

As shown in FIG. 1B, an atrial pulse generator 70 and a ventricular pulse generator 72 generate pacing and ATP stimulation pulses for delivery by desired electrodes. The electrode configuration switch 74 (also referred to as switch bank 74) controls which terminals 44-59 receive shocks or pacing pulses. The atrial and ventricular pulse generators, 70 and 72, may include dedicated, independent pulse generators, multiplexed pulse generators, shared pulse generators or a single common pulse generator. The pulse generators 70 and 72 are controlled by the microcontroller 60 via appropriate control signals 76 and 78, respectively, to trigger or inhibit stimulation pulses. The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc.

The switch bank 74 includes a plurality of switches for connecting the desired electrodes to the appropriate I/O circuits, thereby providing complete electrode programmability. The switch 74, in response to a control signal 80 from the microcontroller 60, determines the polarity of the stimulation pulses (e.g., unipolar, bipolar, co-bipolar, etc.) by selectively closing the appropriate combination of switches (not specifically shown). Atrial sensing circuits 82 and ventricular sensing circuits 84 may also be selectively coupled to the right atrial lead 20, LV lead 24, and the right ventricular lead 30, through the switch 74 for detecting the presence of cardiac activity in each of the four chambers of the heart. The switch 74 determines the "sensing polarity" of the cardiac signal by selectively closing the appropriate switches. The outputs of the atrial and ventricular sensing circuits 82 and 84 are connected to the microcontroller 60 which, in turn, is able to trigger or inhibit the atrial and ventricular pulse generators 70 and 72, respectively. The sensing circuits 82 and 84, in turn, receive control signals over signal lines 86 and 88 from the microcontroller 60 for purposes of controlling the gain, threshold, the polarization charge removal circuitry (not shown), and the timing of any blocking circuitry (not shown) coupled to the inputs of the sensing circuits, 82 and 86.

For arrhythmia detection, the device 10 utilizes the atrial and ventricular sensing circuits 82 and 84 to sense cardiac signals and the arrhythmia detection module 75 to determine whether a rhythm is physiologic or pathologic. As used herein "sensing" is the receipt or noting of an electrical signal, and "detection" is the processing of these sensed signals and determining the presence of an arrhythmia. The timing intervals between sensed events (e.g., P waves, R waves, and depolarization signals associated with fibrillation which are sometimes referred to as "F waves" or "Fib waves") are then classified by the microcontroller 60 by comparing them to a predefined rate zone limit (e.g., bradycardia, normal, low rate VT, high rate VT, and fibrillation rate zones) and/or various other characteristics (e.g., sudden onset, stability, physiologic sensors, morphology, etc.) in order to determine the type of remedial therapy that is needed (e.g., bradycardia pacing, antitachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 samples cardiac signals across any pair of desired electrodes. The data acquisition system 90 may be coupled to the microcontroller 60, or other detection circuitry, for detecting an evoked response from the heart 12 in response to an applied stimulus, thereby aiding in the detection of "capture." Capture occurs when an electrical stimulus applied to the heart is of sufficient energy to depolarize the cardiac tissue, thereby causing the heart muscle to contract.

The microcontroller 60 is further coupled to a memory 94 by a suitable data/address bus 96, wherein the programmable operating and therapy-related parameters used by the microcontroller 60 are stored and modified, as required, in order to customize the operation of the stimulation device 10 to suit the needs of a particular patient. The operating and therapy-related parameters define, for example, pacing pulse amplitude, pulse duration, electrode polarity, rate, sensitivity, automatic features, arrhythmia detection criteria, and the amplitude, wave shape and vector of each stimulating pulse to be delivered to the patient's heart 12 within each respective tier of therapy.

The operating and therapy-related parameters may be non-invasively programmed into the memory 94 through a telemetry circuit 100 in telemetric communication with the external device 102, such as a programmer, trans-telephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

The stimulation device 10 may include a physiologic sensor 108 to adjust pacing stimulation rate according to the exercise state of the patient. The physiological sensor 108 may further be used to detect changes in cardiac output, changes in the physiological condition of the heart, or diurnal changes in activity (e.g., detecting sleep and wake states). The microcontroller 60 responds by adjusting the various pacing parameters (such as rate, AV Delay, V-V Delay, etc.) at which the atrial and ventricular pulse generators, 70 and 72, generate stimulation pulses.

The battery 110 provides operating power to all of the circuits shown in FIG. 1B. An impedance measuring circuit 112 monitors lead impedance during the acute and chronic phases for proper lead positioning or dislodgement; detects operable electrodes and automatically switches to an operable pair if dislodgement occurs; measures respiration or minute ventilation; measures thoracic impedance for determining shock thresholds; detects when the device has been implanted; measures stroke volume; and detects the opening of heart valves, etc.

The microcontroller 60 further controls a shocking circuit 116 by way of a control signal 118. The shocking circuit 116 generates stimulating pulses of low (up to 0.5 Joules), moderate (0.5-10 Joules), or high energy (11 to 40 Joules), as controlled by the microcontroller 60. Stimulating pulses are applied to the patient's heart 12 through at least two shocking electrodes, and as shown in this embodiment, selected from the left atrial (LA) coil electrode 29, the RV coil electrode 36, the SVC coil electrode 38 and/or the housing 40.

Figure 2:
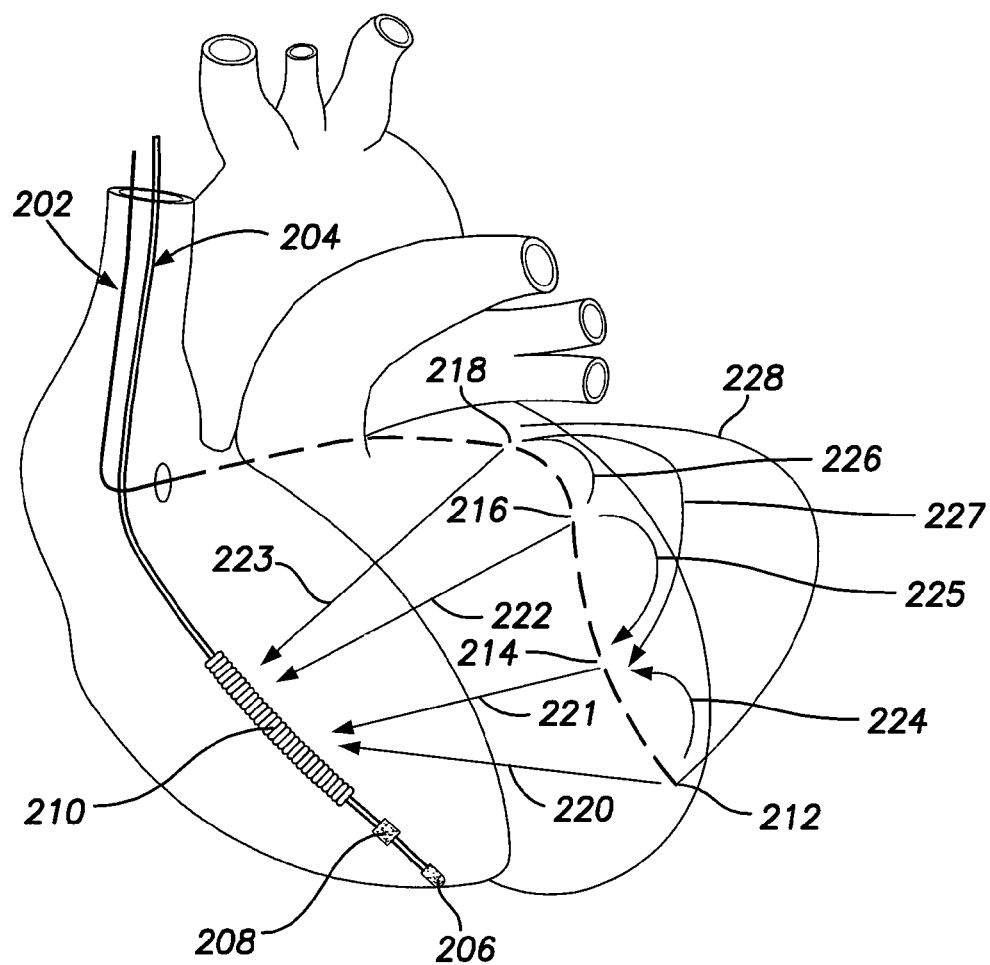
FIG. 2 illustrates a lead configuration utilized in accordance with an embodiment.

FIG. 2 illustrates RV and LV leads utilized in accordance with an embodiment. In FIG. 2, an RV lead 202 and an LV lead 204 are shown. The RV lead 202 includes tip, ring and coil RV electrodes 206, 208 and 210 located in the right ventricle. The RV lead 202 may also include an electrode in the right atrium and/or at the SVC. The LV lead 204 includes a tip LV electrode 212 and (ring) LV electrodes 214, 216 and 218. The LV electrodes 214, 216 and 218 are spaced apart from one another along the lateral wall of the left ventricle. The LV lead 204 may include electrodes proximate to the left atrium.

Optionally, more or fewer LV electrodes may be utilized. Optionally, the LV electrodes may be separated more or positioned closer to one another. Optionally, all or a portion of the LV electrodes may be shifted along the LV lead 204 until positioned proximate to the mitral valve, aortic valve, or the left atrial ports to/from the pulmonary veins. Optionally, the LV lead 204 may be inserted into the LV chamber or inserted into another vein or artery extending along the heart wall proximate to the left ventricle. Optionally, the LV lead 204 may be coupled to a patch or mesh net electrode that is secured to or located adjacent to an exterior wall of the left ventricle and/or the left atrium.

The LV electrodes 212-218 and/or RV electrodes 206-210 are utilized in various combinations to define different sensing and excitation sites and vectors. For example, vectors 220-223 extend between corresponding LV electrodes 212-218 and a common RV (coil) electrode 210. Vectors 224-226 extend between corresponding pairs of adjacent LV electrodes 212-218. Vectors 227 and 228 extend between corresponding pairs of non-adjacent spatially distributed LV electrodes (e.g., 218 and 214, and 218 and 212).

Each LV and RV electrode 206-218 represents a potential sensing site and/or therapy site. When functioning as a sensing site, the corresponding LV and/or RV electrode 206-218 sense cardiac activity at the electrode position. The cardiac activity may represent intrinsic or paced normal sinus rhythms or intrinsic arrhythmic behavior. The cardiac activity may represent electrical activity that results following one or more stimuli that are induced at another site. Each stimulus (induced at one site) causes electrical activity to propagate along an activation pattern through at least a portion of the heart wall. The propagating electrical activity is sensed at RV and LV sensing sites as evoked responses.

Embodiments described herein manage ULV testing for estimation of DFT such that the heart cells that are in the region along the defibrillation vector that will experience the low voltage gradient have re-polarized after a paced beat before a ULV shock is delivered during the vulnerable period of the T wave. Pacing from the proximity of ULV shocking electrode may not yield the desired re-polarization timing sequence to mimic defibrillation and in turn estimate the DFT. Embodiments are described herein that seek to control the re-polarization timing sequence through a different pacing scheme, namely a pacing scheme originating at an LV electrode that is estimated to be located proximate to a heart region along the defibrillation vector that exhibits a desired local conduction property. In an embodiment, the local conduction property corresponds to a local voltage gradient for an electric field distribution of a defibrillation shock, which is low relative to the local voltage gradient in other regions of the heart. When the ULV pacing pulse is delivered in the heart region having the desired local conduction property (e.g., lowest voltage gradient) relative to the ULV shocking electrode, it is believed that such a pacing scheme would provide consistent and reliable DFT estimation, especially in the patients having high DFTs. Embodiments of the new methods and systems for finding ULV are discussed in detail herein.

Figure 3B:
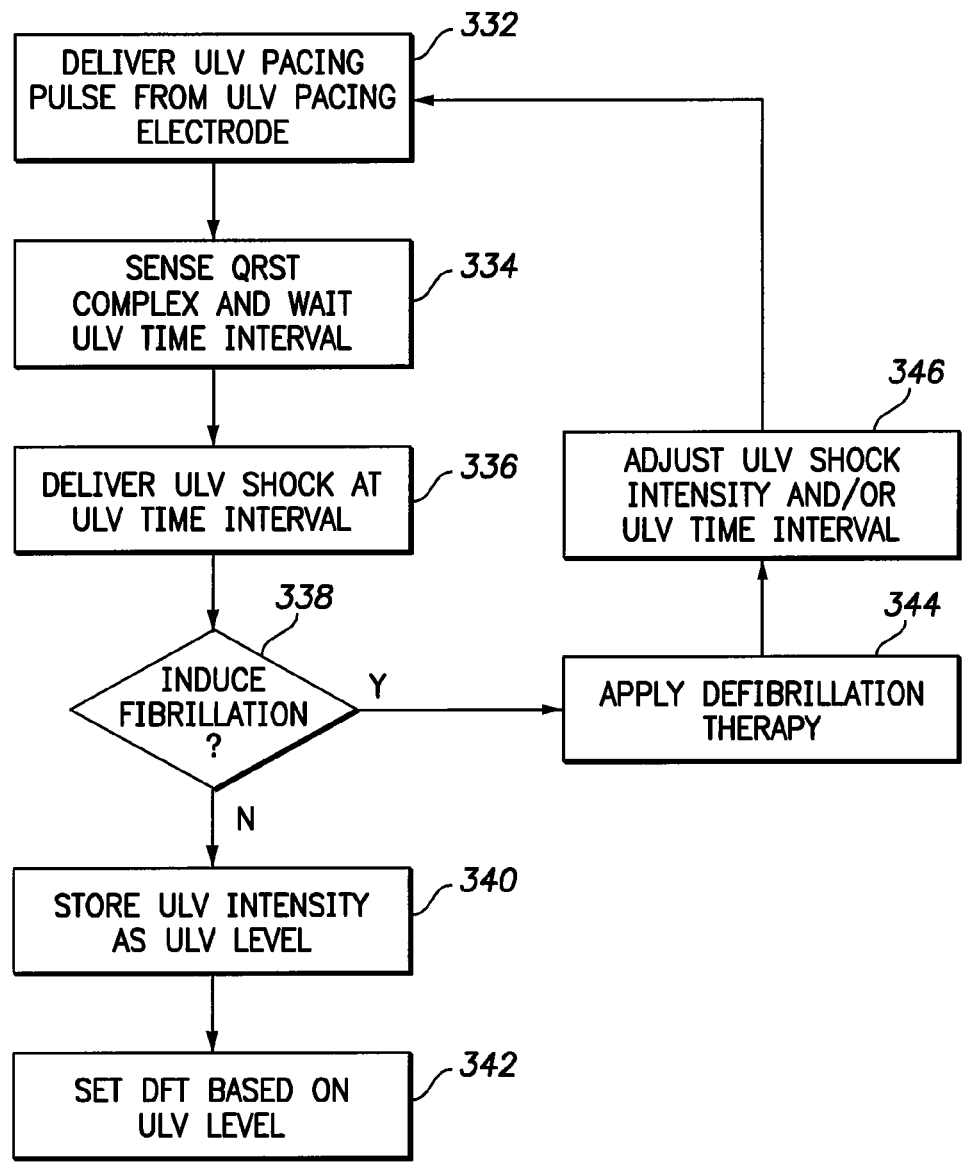

FIGS. 3A and 3B illustrate DFT estimation processing sequence carried out in accordance with an embodiment of the present invention.

Figure 4:
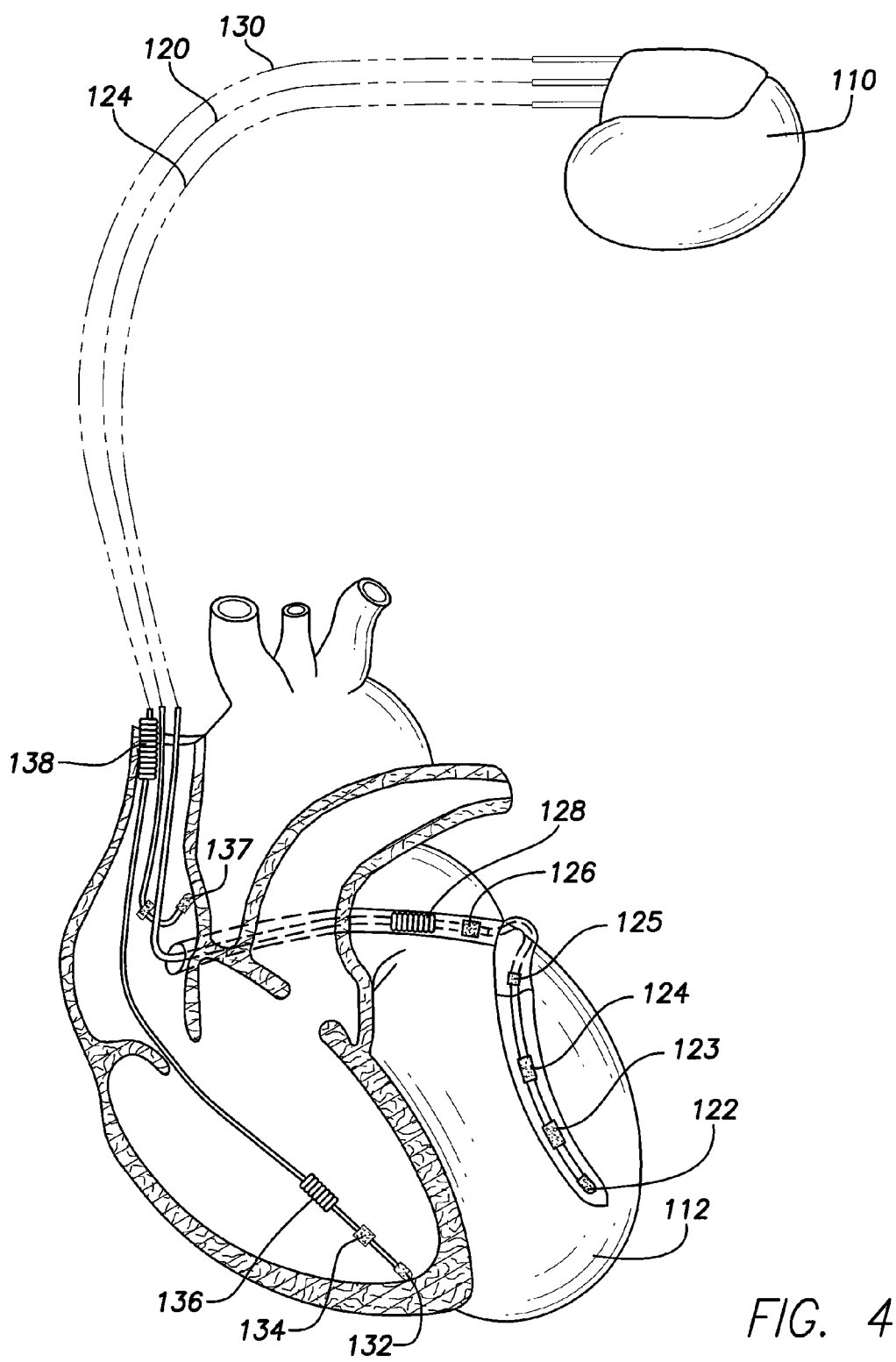
FIG. 4 illustrates an exemplary configuration of leads and electrodes that are used to explain the process of FIGS. 3A and 3B.

FIG. 4 illustrates an exemplary configuration of leads 120, 124 and 130 and electrodes 122 to 138 that are used to explain the process of FIGS. 3A and 3B. FIG. 3A concerns a process to determine the ULV pacing electrode and set up the parameters for the ULV test. FIG. 3B concerns a ULV test process to estimate DFTs. In FIG. 3A, at 302, the process automatically searches for a pacing threshold at one or more electrodes that perform pacing and/or sensing. The search for the pacing threshold may represent a capture determination process that automatically follows a paced event, whereby it is determined whether the pacing stimulus was sufficient to achieve capture. The pacing threshold may be determined at one or more of LV electrodes 122-126.

At 304, the process delivers a pacing stimulus to the heart from a non-pacing, shocking electrode. The shocking electrode represents an electrode that is generally configured to deliver stimulus pulses with an energy level that is greater than the energy level of a pacing pulse, such as a defibrillation electrode. For example, in FIG. 4, the non-pacing shocking electrode may be the RV electrode 132. Alternatively, the non-pacing shocking electrode may be the RV electrode 136, the RV electrode 134, and/or one or more of the LV or LA electrodes 122-128.

At 306, the process senses LV signals that are responsive to the pacing stimulus delivered at 304. The LV signals are sensed by at least one LV electrode that is located proximate to the left ventricle. For example, the LV signals may represent voltage potentials measured in volts, millivolts, amps or milliamps. With reference to FIG. 4, LV electrode 122 may measure a first voltage potential, while the LV electrodes 123, 124 and 125 each separately measure second, third and fourth voltage potentials, respectively, that each differ from one another. When the pacing stimulus is delivered from the RV tip electrode 132, the voltage potential of the LV signal measured at the LV electrode 122 may be greater than the voltage potential measures at the LV electrodes 123, 124 and 125. Similarly, the voltage potential measured at each of the LV electrodes 123, 124 and 125 may progressively decrease the further in distance from the pacing RV electrode 132. Alternatively, if the pacing stimulus is delivered by a RA electrode 137 or a LA electrode 128 or 126, the voltage potential of the LV signal measured at the LV electrode 125 may be greater than the voltage potential measures at the LV electrodes 124, 123, and 122. The voltage potential measured at each of the LV electrodes 124, 123 and 122 may progressively decrease the further in distance from the pacing electrode.

At 308, the process obtains local conduction (LC) information based on the LV signals sensed by the LV electrodes 122-125. The LC information may include local voltage gradients (e.g., measured in volts per centimeter), amperage gradient information (e.g., measured in amps per centimeter) or power distribution (e.g., measured in Joules or watts per centimeter). The LC information is associated with the heart tissue that is located immediately proximate to the corresponding LV electrodes 122-125 at which LV signals are sensed. To calculate a local voltage gradient, first the process determines the peak voltage in each LV signal that is measured by the corresponding LV electrode during a sensing period of time. Next, the process calculates the voltage difference between the peak voltages. For example, a voltage difference $V_{LV122\text{-}LV123}$ may be calculated between the measured peak voltage $VL_{122}$ at LV electrode 122 and the measured peak voltage $VL_{123}$ at LV electrode 123. A voltage difference $V_{LV124\text{-}LV125}$ may be calculated between the measured peak voltage $VL_{124}$ at LV electrode 124 and the measured peak voltage $VL_{125}$ at LV electrode 125. For example, when a pacing stimulus is delivered by RV electrode 132, a local voltage gradient of 12V/cm may be calculated between LV electrodes 122 and 123, while a local voltage gradient of 8V/cm may be calculated between LV electrodes 124 and 125.

Optionally, the voltage from the LV signals measured at the LV electrodes 122-126 may not represent peak voltages, but instead represent averages, medians, or some other statistical representation of voltage at a desired feature in the cardiac signal.

Once the voltage difference is obtained between two LV electrodes, the voltage difference is then divided by the physical distance between the corresponding LV electrodes that measured the voltages. For example, the voltage difference $VL_{122}\text{-}LV_{123}$ is divided by a distance $D_{LV122\text{-}LV123}$ between the LV electrodes 122 and 123 to thereby determine the local voltage gradient at or between LV electrodes 122 and 123. Similarly, the voltage difference $VL_{124}\text{-}LV_{125}$ is divided by a distance $D_{LV124\text{-}LV125}$ between the LV electrodes 124 and 125 to thereby determine the local voltage gradient at or between LV electrodes 124 and 125.

The physical distances (e.g., measured in centimeters or inches) between any and all desired combinations of LV electrodes are stored in an external device or in the IMD. The physical distances may be prerecorded before implant or programmed by a physician or technician at the time of implant or post-implant. For example, the IMD or external device may store the distance $D_{LV122\text{-}LV123}$ between adjacent electrodes 122 and 123 in centimeters or inches. Similarly, the IMD or external device may store distances between adjacent LV electrodes 123 and 124, and between adjacent LV electrodes 124 and 125.

Also, the IMD or external device may store distances between remote, non-adjacent LV electrodes. For example, the IMD or external device may store the distances between one or more combinations of non-adjacent LV electrodes 122 and 124, LV electrodes 122 and 125, and LV electrodes 123 and 125. Optionally, the IMD or external device may store a distance between non-LV electrodes and LV electrodes, when it is desirable to calculate voltage gradients therebetween. For example, the IMD or external device may store the distance between RV electrode 132 and one or more of the LV electrodes 122-125, and/or the distance between RA electrode 137 and one or more of the LV electrodes 122-125, and/or any other electrode combinations that can be used to calculate LC information, such as the local voltage gradient. The low voltage gradient regions associated with common defibrillation vectors used clinically (e.g., Active CAN+SVC-RV or Active CAN-RV) are LV apex and posterior or anterior LV free wall in the patients with normal cardiac dimension or mainly in posterior LV free wall for patients with large LV hearts. Once the LC information (e.g., voltage gradient) is calculated for multiple LV electrode combinations at 308, flow moves to 310.

At 310, the process estimates a shock intensity for one or more ULV shocks. The ULV shock(s) may be delivered by one or more RV electrodes, by one or more RA electrodes and the like. The ULV shock intensity may be preprogrammed manually or automatically determined based on the strength of the LV signals sensed at the LV electrodes at 306. An initial ULV shock strength may be set based on the pacing threshold determined at 302. For example, the diastolic pacing threshold (PTH_dia) may be increased by a predetermined multiple (X) to set the initial ULV shock intensity shock_start for the shocking electrode (e.g., RV electrode 132): shock_start=X*PTH_dia where X=2 or other.

Alternatively, the ULV shock strength may be determined utilizing the local conduction information from the LV electrodes. For example, at 304, when the RV electrode 132 delivers a pacing pulse of Y volts, the LV electrode 123 may sense an evoked response of Z Volts. If the pacing threshold for the LV electrode 123 is measured to be TH_LV, the estimated ULV shock intensity could be set at or near $ULV_{Shock\ Est}$=FCTR*TH_LV/Z*Y. The value FCTR represents a factor that can be set based on a ratio of the refractory pacing threshold (when the tissue at the LV electrode is in a refractory state) to the diastolic pacing threshold (when the tissue at the LV electrode is in a diastolic state). If an RV lead is the only lead available, the same technique could be used. For example, one electrode on the RV lead would be used to deliver a pacing pulse and another RV electrode would be used to sense.

At 312, the process designates at least one electrode to be a ULV pacing electrode. For example, the ULV pacing electrode may be one of LV electrodes 122-125. The electrode designated to be the ULV pacing electrode is the electrode located proximate to the region of the heart for which the LC information satisfies one or more predetermined LC characteristics. For example, when the LC information includes local voltage gradient (LVG) information, the predetermined LC characteristic may represent the lowest voltage gradient. Thus, at 312, the LV electrode(s) are designated that are located closest to the heart region that exhibits the lowest voltage gradient.

For example, the voltage gradient between LV electrodes 124 and 125 may be determined to be 8V/cm, while the voltage gradient between LV electrodes 122 and 123 may be determined to be 12V/cm. In this example, one or both of the LV electrodes 124 and 125 would be designated to satisfy one or more of the predetermined LC characteristics, namely the lowest local voltage gradient. As a further example, the voltage gradient between LV electrodes 123 and 124 may be determined to be 7V/cm, while the voltage gradient between LV electrodes 122 and 124 may be determined to be 8V/cm. In this example, the LV electrode 124 would be designated to correspond to the lowest local voltage gradient. In the foregoing manner, the ULV pacing electrode is identified.

At 314, the process performs overdrive pacing to the heart from the ULV pacing electrode. The pacing rate is higher than the intrinsic rate, when overdrive pacing the heart. The region of the heart, for which the LC information satisfies the predetermined LC characteristic, becomes re-polarized early in a repolarization phase following pacing of the heart. By pacing in the region of interest having a predetermined local conduction characteristic, such as a low voltage gradient, this allows the cells in the LVG region of interest to become re-polarized first before the cells in other regions of the heart. In the above examples, the LVG region of the heart is paced by a LV electrode. Optionally, the low voltage gradient region of the heart may be paced by a cutaneous electrode through an external pacemaker/defibrillator during the implantation process or post-implant.

At 316, the process identifies the R and/or T wave that will be uses as the basis for subsequent ULV shocks. The T wave may be detected from an RV electrode, an RA electrode, an LV electrode, an IEGM electrode or elsewhere. The T wave peak location may be located automatically by an external device or the IMD, such as through peak detection, a running average, and the like. Alternatively, the T wave peak may be found indirectly by first determining the ventricular effective refractory period (VERP) as explained below in connection with FIG. 5.

At 318, the ULV time interval is set up based on the R wave and/or T wave sensed by the ULV shocking electrode. When the T wave is used as the reference time from which ULV shocks are delivered, the ULV time interval may be set as a predetermined time increment in milliseconds, such as 20 ms, 40 ms, 50 ms, etc. longer than the VERP. When the R wave is used as the reference time from which ULV shocks are delivered, the ULV time interval may be scheduled to correspond to the VERP plus the predetermined additional time increment (e.g., 20 ms, 40 ms, 50 ms, etc.).

At 320, the ULV shocking intensity is set up automatically. For example, the ULV shocking intensity may be initially set to a programmed energy level. The ULV shocking intensity may be incremented by programmed predetermined steps. Once 320 is complete, flow moves to FIG. 3B where ULV shocks are delivered.

In FIG. 3B, at 332, a new ULV pacing pulse is delivered from the ULV pacing electrode or electrodes. At 334, the QRST complex is sensed at the ULV shocking electrode or at another electrode. The peak of the R wave and/or the peak of the T wave are identified as explained above.

At 336, the ULV shocking electrode(s) deliver a ULV test shock at the ULV time interval relative to the R wave and/or T wave. For example, the ULV shocking electrode(s) may be the RV electrode 132, the RV electrode 136, the RA electrode 138, the LA electrode 128 and the like.

At 338, the process monitors the heart for ventricular fibrillation. If the ULV shock delivered at 336 is at an energy level at or about the physiologic ULV for the patient, then the ULV shock will not induce fibrillation. When defibrillation is not induced at 336, flow moves to 340 where the ULV shock level is stored as the patients ULV level. However, when the ULV shock at 336 is at an energy level below the ULV for the patient, then the physiologic ULV shock will induce fibrillation. When fibrillation is induced at 336, flow moves to 344.

At 344, a defibrillation therapy is delivered. The defibrillation therapy may involve one or more high energy shocks as necessary to defibrillate the heart.

At 346, the process adjusts the ULV shock intensity and/or the ULV time interval. For example, the ULV shock intensity may be increased by a programmed energy step (e.g., 5 Joules). Optionally, the ULV time interval may be adjusted by a programmed time step (e.g., changed between −40 ms, 20 ms, 0, +20 ms, +40 ms, etc.) with respect to the peak of the T wave.

Returning to 332, the heart is paced again from the LV electrode(s) identified to be proximate to the heart region having the local conduction characteristic of interest (e.g., low voltage gradient region).

At 334, a new cardiac signal is sensed and the timing reference feature of interest is identified, such as the peak of the R wave or the peak of the T wave. Next, at 336 another ULV shock is delivered at the ULV time interval.

At 346, one or both of the ULV intensity and ULV time interval may be adjusted each iteration or during different iterations. For example, after first and second ULV shocks, only the ULV time interval may be changed. After a third ULV shock, the ULV time interval may be reset to the initial ULV time interval and the ULV shock intensity adjusted. In the foregoing manner, ULV shocks may be delivered at different times relative to the T wave and at different intensities. The process of FIG. 3B is repeated until a ULV level is identified and stored at 340. Then the process moves to 342.

At 342, the DFT is set based on the ULV level. The DFT may be determined to be equal to, or a predetermined amount greater than, the ULV level. For example, the DFT may be set X Joules greater than the ULV level. Optionally, the DFT may be set as a factor times the ULV Level.

Figure 5:
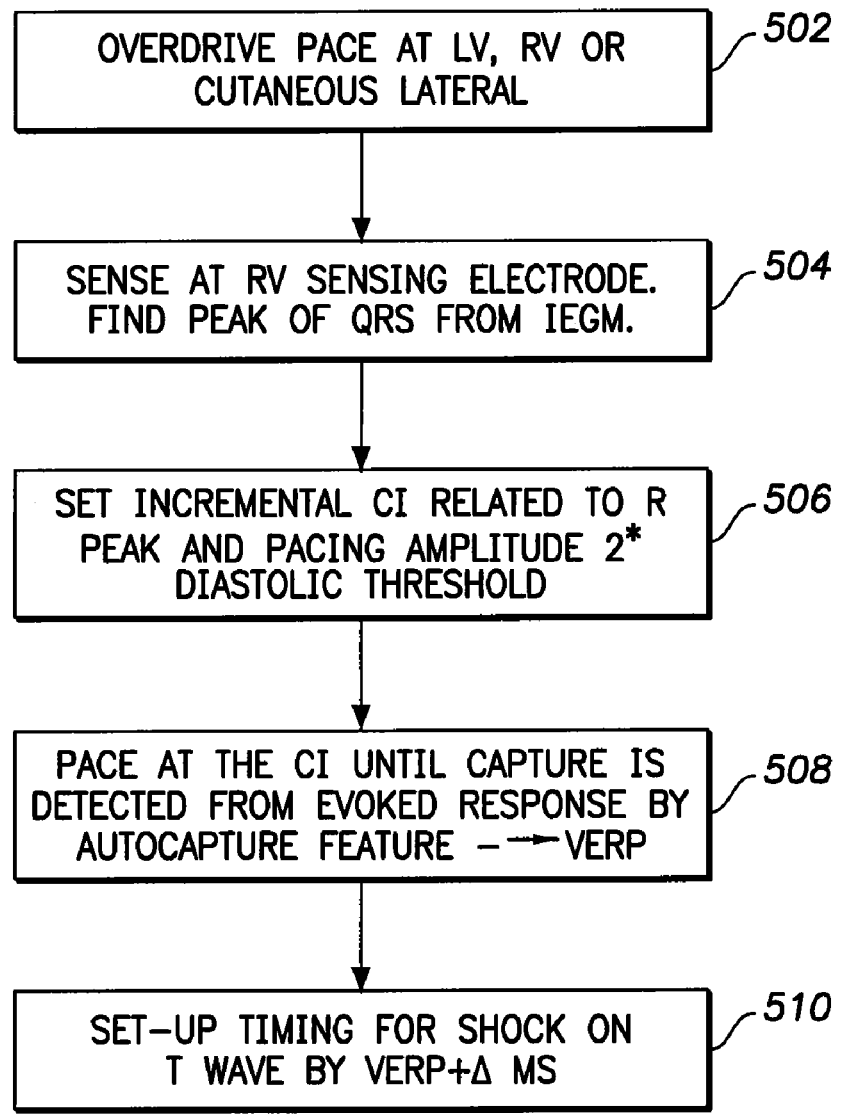
FIG. 5 illustrates a flow chart for a processing sequence to automatically determine the ULV test interval based on the ventricular effective refractory period in accordance with an embodiment.

FIG. 5 illustrates a flow chart for a processing sequence to automatically determine the ULV time interval based on the ventricular effective refractory period in accordance with an embodiment of the present invention. At 502, an LV electrode or a cutaneous electrode are used to pace the heart at an overdrive rate (e.g., faster than the intrinsic heart rate). At 504, an RV electrode is used to sense the cardiac signal for a feature of interest, such as a peak in the QRS complex. At 506, a programmed delay is set at a constant interval (CI) relative to the peak of the R wave. Also at 506, a pacing amplitude is set as a factor of the diastolic pacing threshold (e.g., 2*Dia_Thr).

At 508, a scheduled pacing pulse is delivered at the constant interval following an R wave. If an evoked response is not detected, the process increments the CI delay relative to the peak of the R wave and another pacing pulse is delivered at the new programmed CI delay following the peak of the next R wave. The process is repeated (namely pace, sense, change CI) until an evoked response is detected. Once an evoked response is detected, the current CI delay from the peak of the R wave represents the ventricular effective refractory period (VERP). At 510, the effective T wave may be set to follow the R wave peak by the VERP plus an amount ΔMS.

Figure 6:
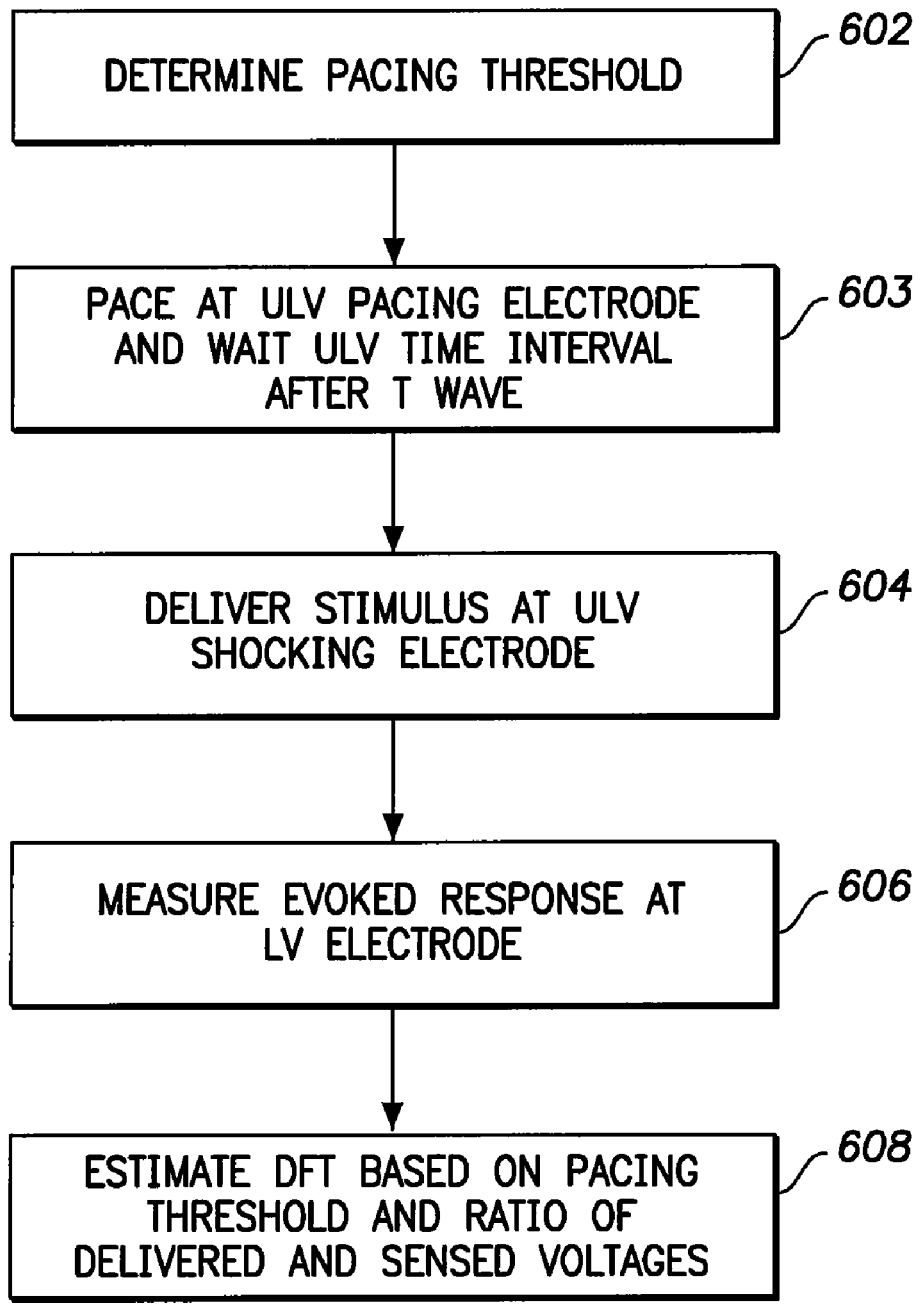
FIG. 6 illustrates a flow chart for a fibrillation-avoided DFT estimation sequence to automatically determine the DFT based on one or more shocks without inducing fibrillation.

FIG. 6 illustrates a flow chart for a fibrillation-avoided DFT estimation sequence to automatically determine the DFT based on one or more shocks without inducing fibrillation. The process of FIG. 3A may still precede the process of FIG. 6.

At 602, the process automatically searches for a pacing threshold at the LV electrode(s) that may be utilized during the ULV-based DFT estimation. For example, a capture determination process may be used to automatically search for the pacing threshold following a paced event. For example, the pacing threshold may be determined at LV electrodes 122-125.

At 603, the heart is paced by the ULV pacing electrode in the region of the heart, for which the LC information satisfies the predetermined LC characteristic (as determined at 312 in FIG. 3A). Thus, the region surrounding the ULV pacing electrode becomes re-polarized first in a repolarization phase following pacing of the heart as compared to other regions of the heart further from the pacing site.

At 604, a stimulus is delivered from a non-pacing, shocking electrode. The stimulus may be delivered at a pacing energy level (e.g., a few volts) or at a higher non-pacing shocking level (e.g., 400-700 volts, or 500 volts). For example, the non-pacing shocking electrode may be the RV electrode 132. At 606, LV signals are sensed that are responsive to the stimulus delivered at 604. The LV signals are sensed by at least one LV electrode that is located proximate to the left ventricle. For example, the LV signals may represent voltage potentials measured in volts, millivolts, amps or milliamps. The measured LV signals are used as, or in connection with obtaining, local conduction information for the local region of the heart.

At 608, a DFT estimate is calculated based on the local conduction information and the formula: DFTShock Est=FCTR*TH_LV/Z*Y volt. The value Y represents the voltage of the stimulus delivered at 604 to the RV electrode 132. The value Z represents the voltage measured at the LV electrode (e.g., in volts). The value TH_LV represents the pacing threshold measured at the LV electrode. The value FCTR represents a factor that can be set based on a ratio of the refractory pacing threshold (when the tissue at the LV electrode is in a refractory state) to the diastolic pacing threshold (when the tissue at the LV electrode is in a diastolic state). The DFT estimation method of FIG. 6 independently estimates the DFT without inducing fibrillation.

Figure 7:
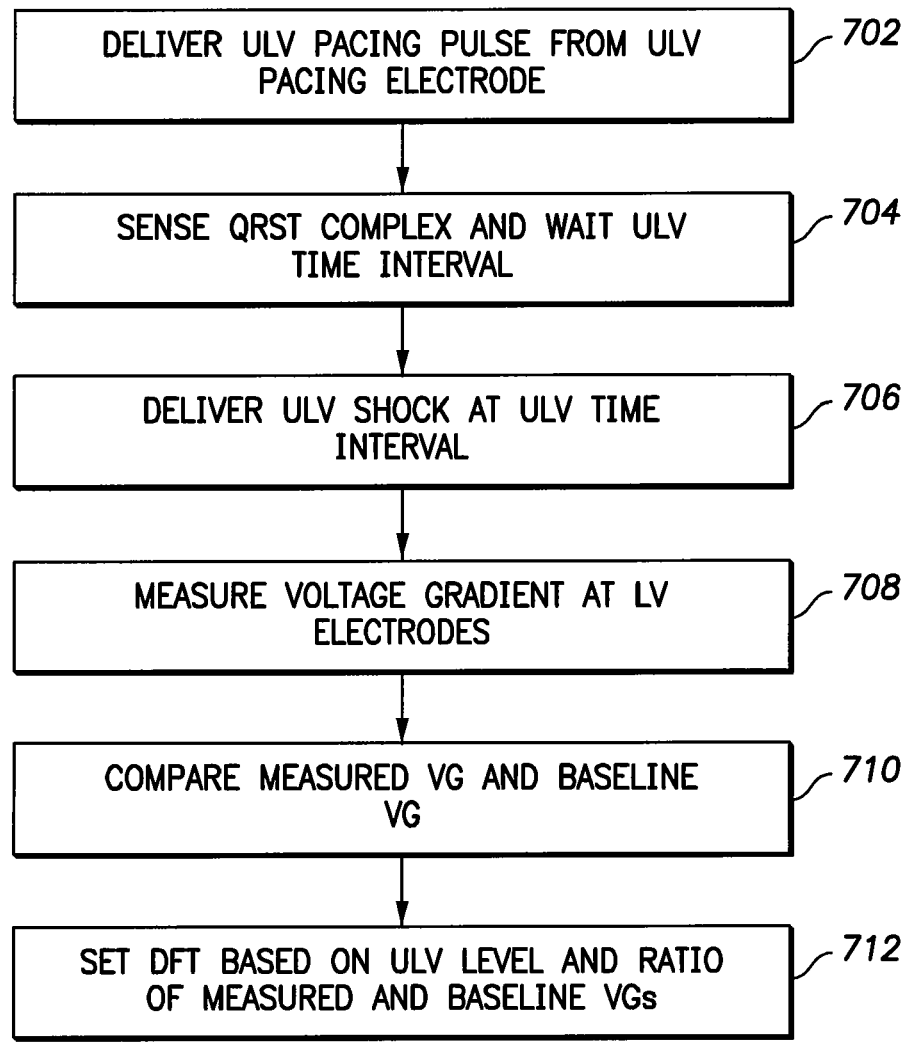
FIG. 7 illustrates a flow chart for an alternative fibrillation-avoided DFT estimation sequence to automatically determine the DFT based on one or more shocks without inducing fibrillation.

FIG. 7 illustrates a flow chart for an alternative fibrillation-avoided DFT estimation sequence to automatically determine the DFT based on one or more shocks without inducing fibrillation. The process of FIG. 3A may be performed initially to set up the process of FIG. 7. For example, in the process of FIG. 3A, a pacing threshold(s) is determined at one or more LV electrodes, local conduction information is obtained and used to designate at least one LV electrode as an ULV pacing electrode, and ULV shock intensity and the ULV time interval are set.

At 702, a new ULV pacing pulse is delivered from the ULV pacing electrode or electrodes. At 704, the QRST complex is sensed at the ULV shocking electrode (e.g., an RV electrode). The peak of the R wave and/or the peak of the T wave are identified, such as based on the determination at 316 in FIG. 3A as explained above. At 706, the ULV shocking electrode(s) deliver a ULV test shock at the ULV time interval relative to the R wave and/or T wave. For example, the ULV shocking electrode(s) may be the RV electrode 132, the RV electrode 136, the RA electrode 138, the LA electrode 128 and the like.

At 708, the process measures the voltage gradient VG across at least two LV electrodes (e.g., 122 and 123). The measured VG at 708 represents an actual voltage gradient in the LV free wall or LV apex at the vulnerable time in the cardiac cycle. The VG will vary from patient to patient due in part to the health of the heart tissue in the posterior and anterior LV wall. The measure VG represents at least part of the local conduction information of the region of the heart near the LV electrode(s).

At 710, the measured VG is compared to a baseline voltage gradient for the left ventricle to produce a measured to baseline VG ratio. The ratio may also represent part of the local conduction information. The baseline VG may be stored in memory at the time of manufacture or programmed by a physician at the time of implant or post-implant. At 712, the VG ratio may be used to set the DFT estimate. For example, a ULV test shock maybe delivered at 16 Joules, the measured VG may be 8V/cm and the baseline VG may be 5V/cm. In this example, the DFT estimate would be 10J (i.e. 10J=16J*(5/8)).

In the above examples, LV electrodes are utilized. Optionally, a cutaneous patch or pad electrode may be positioned at the LV apex and/or along the LV free wall. The cutaneous electrode may be joined to an external pacer or to an IMD. The cutaneous patch or other type can be used for LV pacing in combination of external rescue defibrillator by positioning the patch in the lateral location on the body. By selecting an appropriate size of the patch electrode and setting the shock amplitude low enough for pacing, cutaneous pacing on the LV apex or free wall can be achieved.

The methods and systems described above give an automated procedure for the DFT testing. The IMD has the capability to perform auto pacing threshold searches and auto capture features. The IMD has two channel for pacing and one channel for sensing that is switchable from RV to LV leads. As explained above, the T wave detection feature and VERP may be added to the IMD. Optionally, the cutaneous patch may be used with or in place of an LV lead.

The above description is provided in connection with ventricular DFT estimation. Optionally, embodiments may be implemented in connection with atrial DFT estimation. For example if Can-RV or Can+SVC-RV is the shocking vector, pacing can be delivered from an electrode proximate to or inside the coronary sinus CS. For example, CS electrodes may be placed in or proximate to the coronary sinus. The CS electrodes are used to measure voltage potentials and determine a lowest local voltage gradient (LVG) in the atria. The CS electrode proximate to the lowest LVG is then designated as the ULV pacing electrode and is used during the ULV process of FIGS. 3A and 3B to estimate an atrial DFT.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A method to determine a defibrillation threshold (DFT), comprising:

determining local conduction (LC) information for at least one LV region of the heart;

designating a ULV pacing electrode from a plurality of LV electrodes, where the ULV pacing electrode is located proximate to a region of the heart for which the LC information satisfies a predetermined LC characteristic;

pacing the heart from the ULV pacing electrode such that the region of the heart, for which the LC information satisfies the predetermined LC characteristic, becomes re-polarized early in a repolarization phase following pacing of the heart;

delivering a ULV shock;

obtaining upper limit of vulnerability (ULV) information based on a heart response to the ULV shock; and obtaining a DFT based on the ULV information.

2. The method of claim 1, wherein the determining calculates at least one local gradient associated with at least one region of the heart.

3. The method of claim 1, wherein the determining calculates at least one local gradient that represents voltage per unit distance.

4. The method of claim 1, wherein the ULV and DFT are obtained without inducing fibrillation.

5. The method of claim 1, further comprising:

delivering a stimulus to the heart;

sensing by at least one LV electrode located proximate to the left ventricle, left ventricular (LV) signals that are responsive to the stimulus delivered to the heart.

6. The method of claim 1, further comprising setting a ULV time interval relative to a feature of interest in the cardiac cycle.

7. The method of claim 1, wherein the ULV pacing electrode represents an LV electrode located proximate to the region of the left ventricle that exhibits a local voltage gradient that satisfies the predetermined LC characteristic.

8. A method to determine a defibrillation threshold (DFT) without inducing fibrillation, comprising:

selecting, from a plurality of available electrodes, an LV electrode that is located proximate to a region of the left ventricle free wall or apex;

delivering a ULV shock from at least one of a RV electrode and an RA electrode;

determining local conduction (LC) information based on measurements at the LV electrode; and obtaining a DFT estimate based on the LC information without inducing fibrillation.

9. The method of claim 8, wherein the determining calculates a local gradient associated with at least one region of the heart.

10. The method of claim 9, further comprising forming a ratio between the local gradient and a baseline local gradient, the DFT estimate being set based on a ULV shock intensity and the ratio.

11. The method of claim 1, wherein the LC information represents a voltage level of an evoked response in LV signals sensed by LV electrodes.

12. The method of claim 11, wherein the DFT estimate is obtained based on the voltage level in the LC information and a pacing threshold at the LV electrode.

13. The method of claim 1, wherein the LC information is measured utilizing a multi-electrode LV lead.

14. A system to determine a defibrillation threshold (DFT), comprising:

an input to receive left ventricular (LV) signals measured by an LV electrode;

a processor module configured to determine local conduction (LC) information for at least one LV region of the heart based on the LV signals measured;

a ULV pacing electrode located proximate to a region of the heart for which the LC information satisfies a predetermined LC characteristic;

the processor module configured to control pacing of the heart from the ULV pacing electrode such that the region of the heart, for which the LC information satisfies the predetermined LC characteristic, becomes re-polarized early in a repolarization phase following pacing of the heart;

the processor module configured to control delivery of a ULV shock;

the process module configured to obtain an upper limit of vulnerability (ULV) information based on a heart response to the ULV shock; and the processor module configured to obtain a DFT based on the ULV information.

15. The system of claim 14, wherein the processor module calculates at least one local gradient associated with at least one region of the heart.

16. The system of claim 14, wherein the processor module calculates at least one local gradient that represents voltage per unit distance.

17. The system of claim 14, further comprising:

a shocking electrode to deliver a stimulus to the heart;

at least one LV electrode located proximate to the left ventricle to sense LV signals that are responsive to the stimulus delivered to the heart.

18. The system of claim 14, wherein the processor module sets a ULV time interval relative to a feature of interest in the cardiac cycle.

19. The system of claim 14, wherein the ULV pacing electrode represents an LV electrode located proximate to the region of the left ventricle that exhibits a local voltage gradient that satisfies the predetermined LC characteristic.

20. The system of claim 14, wherein the LC information is measured utilizing a multi-electrode LV lead.

* * * * *